(12) United States Patent
Ashton

(10) Patent No.: US 12,320,007 B1
(45) Date of Patent: Jun. 3, 2025

(54) METHOD FOR MAKING PROSTHETIC DEVICE

(71) Applicant: JointMedica Ltd., Hallow (GB)

(72) Inventor: Roger Ashton, Warwick (GB)

(73) Assignee: JointMedica Ltd., Hallow (GB)

( * ) Notice: Subject to any disclaimer, the term of this patent is extended or adjusted under 35 U.S.C. 154(b) by 0 days.

(21) Appl. No.: 18/956,308

(22) Filed: Nov. 22, 2024

(51) Int. Cl.
  *C23C 24/08* (2006.01)
  *A61F 2/30* (2006.01)

(52) U.S. Cl.
  CPC .......... *C23C 24/087* (2013.01); *A61F 2/3094* (2013.01)

(58) Field of Classification Search
  CPC .......... A61F 2/60; C23C 24/08; C23C 24/087
  See application file for complete search history.

(56) References Cited

U.S. PATENT DOCUMENTS

| | | | |
|---|---|---|---|
| 4,685,923 | A | 8/1987 | Mathys |
| 6,896,703 | B2 | 5/2005 | Barbieri et al. |
| 7,112,301 | B2 * | 9/2006 | Thorne ............ B22F 5/10 419/49 |
| 7,947,083 | B2 | 5/2011 | Ashton et al. |
| 8,277,514 | B2 | 10/2012 | Ashton et al. |
| 8,679,187 | B2 | 3/2014 | Allen et al. |
| 9,017,416 | B2 | 4/2015 | McMinn |
| 9,445,906 | B2 | 9/2016 | Ashton et al. |
| 9,463,093 | B2 | 10/2016 | Allen et al. |
| 9,463,094 | B2 | 10/2016 | Allen et al. |
| 9,649,193 | B2 | 5/2017 | McMinn |
| 10,350,071 | B2 | 7/2019 | Lerf et al. |
| 10,383,745 | B2 | 8/2019 | Allen et al. |
| 10,966,837 | B2 | 4/2021 | McMinn |
| 11,096,798 | B2 | 8/2021 | Allen et al. |
| 11,589,993 | B2 | 2/2023 | Lerf et al. |
| 11,957,590 | B2 | 4/2024 | Gugler et al. |
| 2011/0166664 | A1 * | 7/2011 | Delfosse ............ A61F 2/34 623/22.15 |
| 2012/0139142 | A1 * | 6/2012 | Van Der Zel ........ A61C 13/082 425/141 |

(Continued)

OTHER PUBLICATIONS

"RM Pressfit: Pioneering, proven & isoelastic" Product Information, Matthys, a company of enovis, Item No. 336.010.121; Jan. 2023.

*Primary Examiner* — Robert A Vetere

(74) *Attorney, Agent, or Firm* — GREENBERG TRAURIG, LLP

(57) ABSTRACT

A method including fabricating a prosthesis core from UHMWPE; positioning the prosthesis core within a pressure vessel; filling the pressure vessel with titanium powder having a D50 particle size that is from 200 to 250 microns to a fill level of at least 110% of the height of the prosthesis core within the pressure vessel; sealing the pressure vessel by positioning a pressure plate in contact with the titanium powder; maintaining the pressure vessel at a heated temperature that is from 150 to 200 degrees Celsius and a pressure that is from 10 to 50 MPa for a time that is from 10 to 600 minutes; cooling the pressure vessel to room temperature including a controlled cooling phase to a step-down temperature at a controlled rate of from 0.1 to 10 degrees Celsius per hour, thereby producing a prosthesis including the prosthesis core and a coating including the titanium powder.

16 Claims, 6 Drawing Sheets

(56) References Cited

U.S. PATENT DOCUMENTS

| | | | |
|---|---|---|---|
| 2013/0177467 A1* | 7/2013 | Gupta | B22F 7/004 228/160 |
| 2021/0145604 A1 | 5/2021 | Allen et al. | |
| 2021/0145605 A1 | 5/2021 | Allen et al. | |
| 2024/0197483 A1 | 6/2024 | Gugler et al. | |

* cited by examiner

METHOD FOR MAKING PROSTHETIC DEVICE

FIELD

This disclosure relates generally to a method for making an implantable prosthetic device. More particularly, this disclosure relates to a method for making a prosthetic device that includes a biocompatible metal coated onto a polymeric material.

BACKGROUND

Joint prosthetics for implantation in the human body often include a portion that is configured to be secured to the body in order to retain the prosthetic in its desired location, as well as a portion that acts as an articular surface within the joint. In some cases, the two portions are made from different materials that are suited to these functions. In such cases, the two materials should adhere securely to one another for the prosthetic to be structurally sound and durable once implanted in the body.

SUMMARY

In some embodiments, a method includes fabricating a prosthesis core from a core material, wherein the core material comprises ultra-high molecular weight polyethylene, wherein the ultra-high molecular weight polyethylene has a weight average molecular weight that is in a range of from 2×106 grams per mole to 3×106 grams per mole; positioning the prosthesis core within a pressure vessel, wherein the prosthesis core has a prosthesis core height within the pressure vessel; filling the pressure vessel with titanium powder, wherein the titanium powder has a D50 particle size that is in a range of from 200 microns to 250 microns, and wherein the titanium powder is filled to at least 110% of the core height; sealing the pressure vessel, wherein the sealing the pressure vessel comprises positioning a pressure plate in contact with the titanium powder; maintaining the pressure vessel at a heated temperature that is in a range of from 150 degrees Celsius to 200 degrees Celsius and a pressure that is in a range of from 10 MPa to 50 MPa for a time period that is in a range of from 10 minutes to 600 minutes; cooling the pressure vessel to room temperature, wherein the cooling comprises: a controlled cooling phase in which the pressure vessel is cooled from the heated temperature to a step-down temperature at a controlled cooling rate, wherein the controlled cooling rate is in a range of from 0.1 degrees Celsius per hour to 10 degrees Celsius per hour, wherein the method produces the prosthesis comprising the prosthesis core and a coating comprising the titanium powder.

In some embodiments, the step of sealing the pressure vessel includes hermetically sealing the pressure vessel such that gases cannot enter or exit the pressure vessel. In some embodiments, the step of sealing the pressure vessel includes non-hermetically sealing the pressure vessel such that gases can enter and exit the pressure vessel.

In some embodiments, after sealing the pressure vessel, the titanium powder acts as a working fluid within the pressure vessel.

In some embodiments, the step-down temperature is in a range of from an ambient temperature to 70 degrees Celsius.

In some embodiments, the cooling also includes a second cooling phase in which the pressure vessel is cooled from the step-down temperature to an ambient temperature at an uncontrolled cooling rate.

In some embodiments, at least a portion of the prosthesis core is sized and shaped to form an articular portion of one of an acetabular cup prosthesis, a glenoid implant, a shoulder prosthesis, a knee prosthesis, an ankle prosthesis, or a toe joint prosthesis. In some embodiments, the articular portion of the acetabular cup prosthesis is sized to articulate with a patient's native femoral head. In some embodiments, the articular portion of the acetabular cup prosthesis is sized to articulate with a prosthetic femoral head of a total hip replacement prosthetic joint.

In some embodiments, the step of maintaining the pressure vessel at the heated temperature comprises maintaining the pressure vessel in an oven that is at the heated temperature. In some embodiments, the method also includes preheating the oven to the heated temperature and placing the pressure vessel in the preheated oven prior to maintaining the pressure vessel at the heated temperature.

In some embodiments, the ultra-high molecular weight polyethylene is vitamin E-enriched.

In some embodiments, a thickness of the prosthesis core is in a range of from 5 millimeters to 9 millimeters. In some embodiments, a thickness of the coating is in a range of from 300 microns to 550 microns.

In some embodiments, particles of the titanium powder that form the coating do not adhere to one another to form a unitary whole.

In some embodiments, the titanium powder has a D50 particle size of 225 microns.

BRIEF DESCRIPTION OF THE DRAWINGS

References are made to the accompanying drawings that form a part of this disclosure and that illustrate embodiments in which the systems and methods described in this Specification can be practiced.

Like reference numbers represent the same or similar parts throughout.

DETAILED DESCRIPTION

Figure 1:
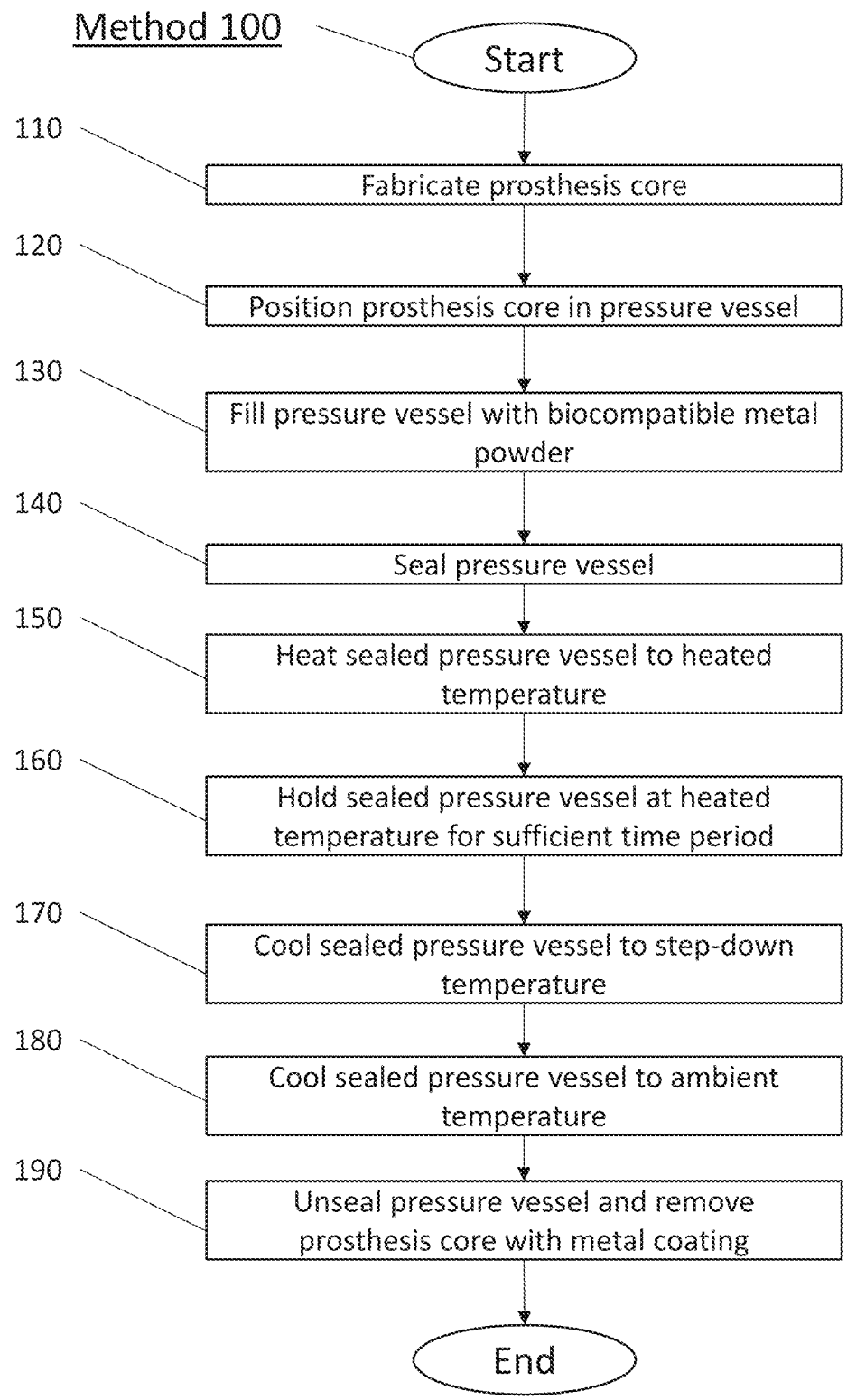
FIG. 1 shows a flowchart of an exemplary process for making a prosthetic device in accordance with some embodiments of the invention.

Embodiments of joint prosthetics for implantation in the human body include a portion that is configured to be secured to the body in order to retain the prosthetic in its desired location, as well as a portion that acts as an articular surface within the joint. In some embodiments, the two portions are made from different materials that are suited to these functions. In some embodiments as described herein, the two materials adhere securely to one another, thereby enabling the prosthetic to be structurally sound and durable once implanted in the body.

In some embodiments, a prosthetic device made in accordance with the exemplary methods described herein includes an articular portion that includes a polymeric material. In some embodiments, as described herein, the articular portion can be referred to as a "core" and the polymeric material can be referred to as a "core material." In some embodiments, the polymeric material includes polyether ether ketone ("PEEK"), polyphenylsulfone ("PPSU"), polyethylene, or a combination thereof. In some embodiments, the polymeric material includes ultra high molecular weight polyethylene ("UHMWPE"). In some embodiments, the UHMWPE has a molecular weight that is in a range of from $2 \times 10^6$ grams per mole to $6 \times 10^6$ grams per mole, or from $2 \times 10^6$ grams per mole to $5 \times 10^6$ grams per mole, or from $2 \times 10^6$ grams per mole to $4 \times 10^6$ grams per mole, or from $2 \times 10^6$ grams per mole to $3 \times 10^6$ grams per mole, or from $2 \times 10^6$ grams per mole to $2.25 \times 10^6$ grams per mole, or from $2 \times 10^6$ grams per mole to $2.5 \times 10^6$ grams per mole, or from $2 \times 10^6$ grams per mole to $2.75 \times 10^6$ grams per mole, or from $2.25 \times 10^6$ grams per mole to $3 \times 10^6$ grams per mole, or from $2.25 \times 10^6$ grams per mole to $2.75 \times 10^6$ grams per mole, or from $2.25 \times 10^6$ grams per mole to $2.5 \times 10^6$ grams per mole, or from $2.5 \times 10^6$ grams per mole to $3 \times 10^6$ grams per mole, or from $2.5 \times 10^6$ grams per mole to $2.75 \times 10^6$ grams per mole, or from $2.75 \times 10^6$ grams per mole to $3 \times 10^6$ grams per mole. In some embodiments, the polymeric material is vitamin E-enriched (e.g., is vitamin E-enriched UHMWPE having a molecular weight that is in a range of from $2 \times 10^6$ grams per mole to $3 \times 10^6$ grams per mole). In some embodiments, the polymeric material includes one of the materials commercialized under the trade name GUR by Celanese Corporation of Irving, Texas.

In some embodiments, a prosthetic device made in accordance with the exemplary methods described herein includes a portion that is made from a biocompatible metal. In some embodiments, the biocompatible metal is a biocompatible metal powder. In some embodiments, the biocompatible metal powder includes titanium. In some embodiments, the biocompatible metal powder includes surgical grade titanium powder that meets the purity standards set out in ASTM F1580-18. In some embodiments, the biocompatible metal powder has a D50 particle size that is in a range of from 200 to 250 microns.

Exemplary methods are described herein with reference to certain apparatuses that are utilized to perform the exemplary methods. The specific apparatuses that are described herein should be understood to be illustrative rather than limiting, and the principles embodied by the exemplary methods can also be practiced through the use of other apparatuses not specifically described herein.

Exemplary methods will be described herein with specific reference to a hip resurfacing prosthesis, which is a prosthesis that is implanted in the pelvis in place of a patient's native acetabulum, and which articulates with a patient's native femoral head. In other embodiments, the exemplary methods may be adapted to make other types of prosthetics, including, but not limited to, an acetabular side of a total hip replacement prosthesis, a portion of a shoulder prosthesis (e.g., a glenoid implant of a shoulder prosthesis), a portion of a knee prosthesis (e.g., a tibial implant of a knee prosthesis), a portion of an ankle prosthesis (e.g., a tibial implant of an ankle prosthesis), or a portion of a toe joint prosthesis (e.g., a metatarsal implant of a toe joint prosthesis, such as a hallux rigidus prosthesis).

Figure 2A:
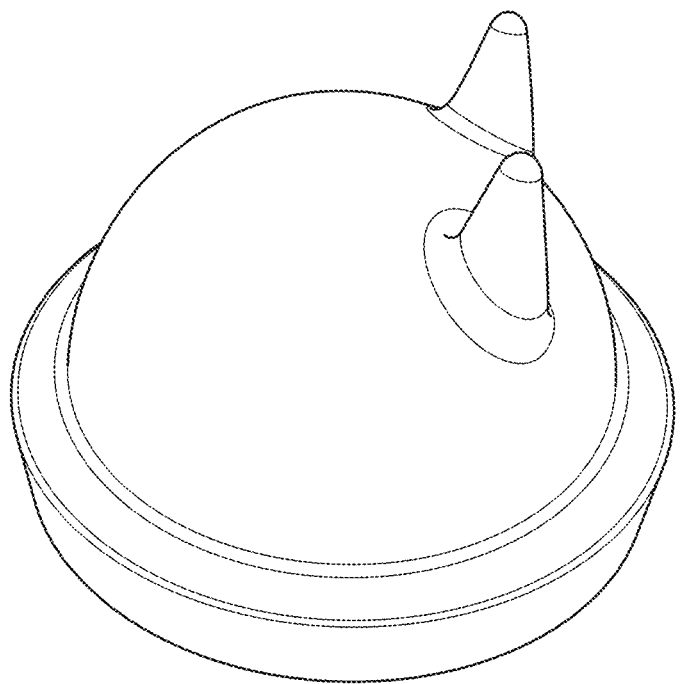
FIG. 2A shows a top perspective view of an exemplary prosthesis core in accordance with some embodiments of the invention.
Figure 2B:
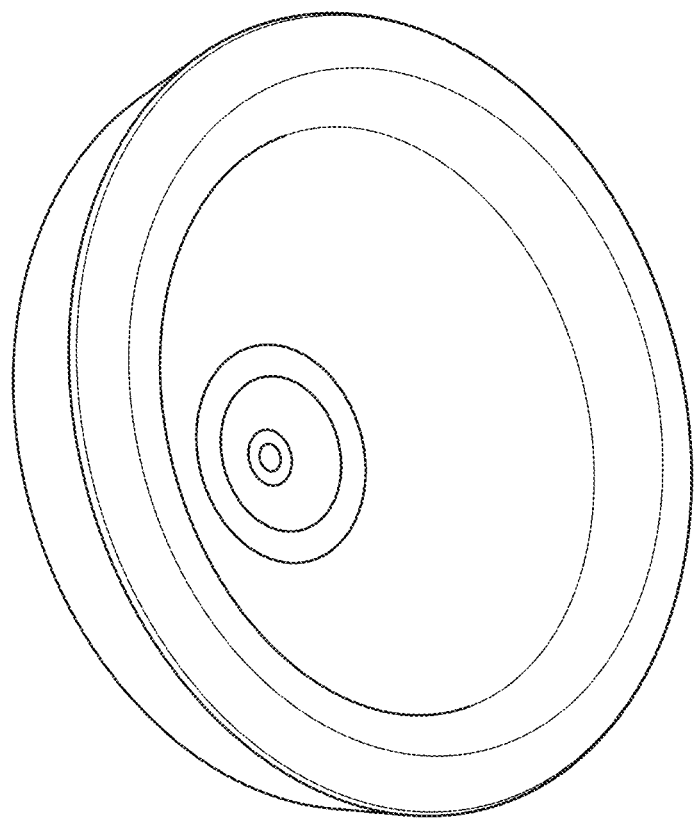
FIG. 2B shows a bottom perspective view of the exemplary prosthesis core shown in FIG. 2A in accordance with some embodiments of the invention.
Figure 2C:
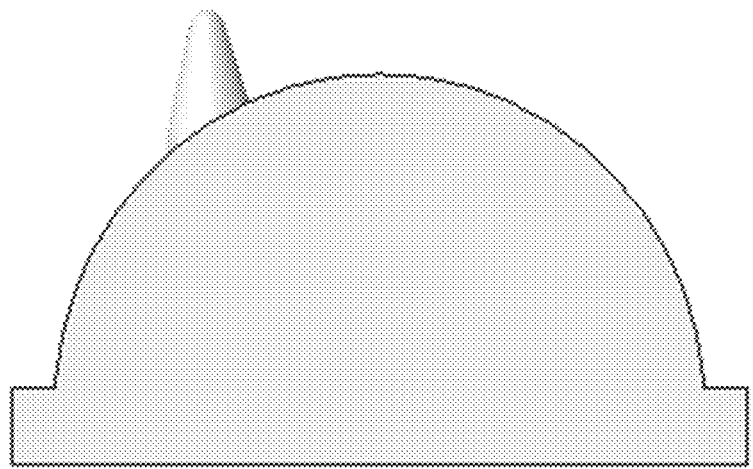
FIG. 2C shows a side view of the exemplary prosthesis core shown in FIG. 2A in accordance with some embodiments of the invention.
Figure 2D:
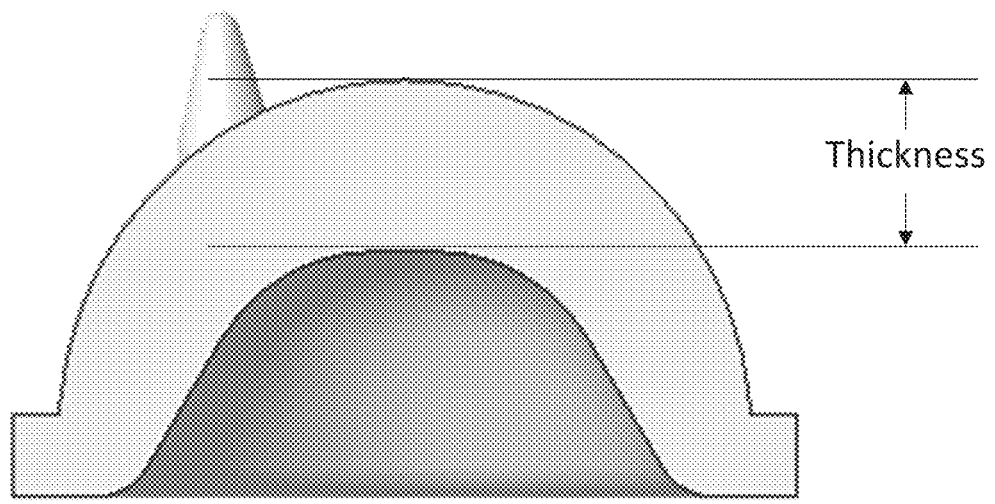
FIG. 2D shows a section view of the exemplary prosthesis core shown in FIG. 2A in accordance with some embodiments of the invention.

FIG. 1 shows a flowchart of an exemplary method 100 for making a prosthetic device by applying a coating to a prosthesis core in accordance with some embodiments of the invention. FIGS. 2A-6 show elements of the prosthetic device and the apparatus for making the same at various stages of the method 100 in accordance with some embodiments of the invention. In step 110, a prosthesis core is formed from a core material. As described above, in some embodiments, the core material is a polymeric material, such as vitamin E-enriched UHMWPE. In some embodiments, the prosthesis core is molded, additively manufactured, machined, or otherwise formed from the core material. FIGS. 2A, 2B, 2C, and 2D show a top perspective view, a bottom perspective view, a side view, and a side section view, respectively, of an exemplary prosthesis core. In some embodiments, the prosthesis core has a thickness (e.g., as measured from an inner surface to an outer surface at the center of the prosthesis core, as shown in FIG. 2D) that is in a range of from 5 millimeters (e.g., for a small size prosthesis) to 9 millimeters (e.g., for a large size prosthesis).

Figure 3:
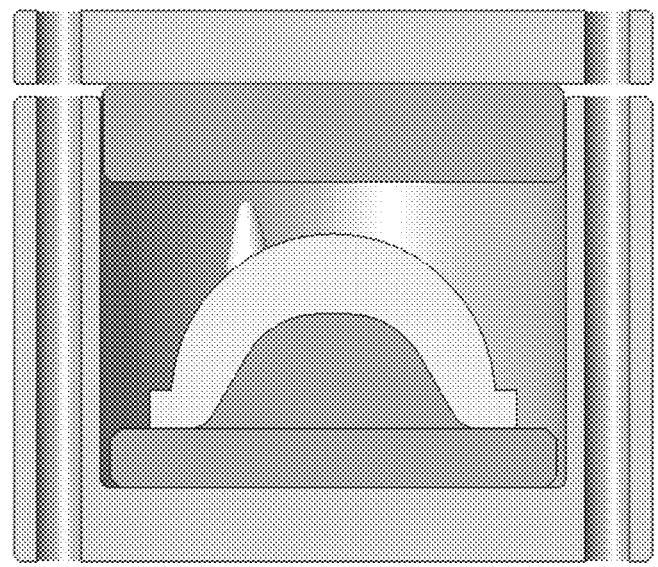
FIG. 3 shows an exemplary prosthesis core as positioned on an exemplary tool within an exemplary pressure vessel in accordance with some embodiments of the invention.

In step 120, the prosthesis core is positioned within a pressure vessel. In some embodiments, the prosthesis core is placed on a tool that is positioned within the pressure vessel. In some embodiments, the tool is sized and shaped to conform to the surface contours of a portion of the prosthesis core. In some embodiments, a contact area between the tool and the prosthesis core defines a portion of the prosthesis core that will remain uncoated during performance of the method 100. For example, in some embodiments, the contact area defines an uncoated portion that is sized and shaped to form an articular surface of an acetabular cup prosthesis. In some embodiments, the pressure vessel includes a base (e.g., an interior bottom surface) upon which the tool is placed. In some embodiments, a non-stick liner is positioned on the tool prior to the prosthesis core to prevent the prosthesis core from sticking to the tool. In some embodiments, the prosthesis core as positioned within the pressure vessel defines a prosthesis core height, which is the distance between the base and the portion of the prosthesis core that is furthest from the base as measured perpendicular to the base. FIG. 3 shows a cross-sectional view of an exemplary prosthesis core positioned on an exemplary tool and within an exemplary pressure vessel in accordance with some embodiments of the invention.

In step 130, the pressure vessel, with the tool and prosthesis core therein, is filled with a biocompatible metal powder. In some embodiments, the biocompatible metal powder is any of the biocompatible metal powders described above. In some embodiments, the biocompatible metal powder is titanium powder having a D50 particle size of 225 microns. In some embodiments, the pressure vessel is filled with a sufficient amount of the biocompatible metal powder so as to fully cover the tool and the prosthesis core, while not being an amount that is excessive such that the biocompatible metal powder interferes with proper sealing of the pressure vessel. In some embodiments, the sufficient amount is an amount that fills the pressure vessel to a height that is at least 110% of the prosthesis core height, where the height to which the biocompatible metal powder fills the pressure vessel is measured from the base and in a direction perpendicular to the base in the same manner as the prosthesis core height.

Figure 4:
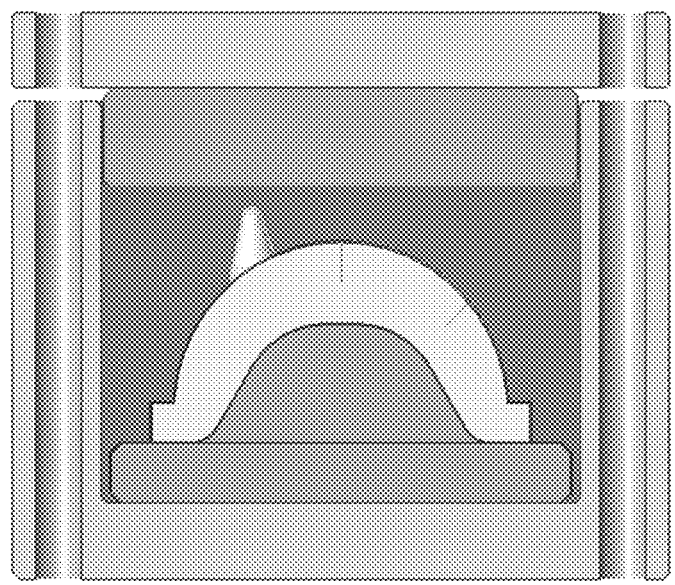
FIG. 4 shows an exemplary prosthesis core as positioned on an exemplary tool within an exemplary pressure vessel, the pressure vessel having been filled with a biocompatible metal powder and sealed, in accordance with some embodiments of the invention.

In step 140, the pressure vessel is sealed. In some embodiments, sealing the pressure vessel includes positioning a pressure plate of the pressure vessel so as to contact the biocompatible metal powder and thereby press down the biocompatible metal powder such that substantially no head space remains between the pressure plate and the biocompatible metal powder. In some embodiments, the sealing is hermetic sealing (e.g., such that gases cannot enter or exit the pressure vessel by flowing into or out of the region enclosed by the pressure vessel and the pressure plate). In some embodiments, the sealing is not hermetic (e.g., non-hermetic) sealing (e.g., such that gases can enter and exit the pressure vessel by flowing into or out of the region enclosed by the pressure vessel and the pressure plate. FIG. 4 shows a cross-sectional view of an exemplary pressure vessel containing an exemplary prosthesis core positioned on an exemplary tool, filled with a biocompatible metal powder and sealed as described above, in accordance with some embodiments of the invention.

In step 150, the sealed pressure vessel is heated to a heated temperature. In some embodiments, the heated temperature is a temperature that is sufficiently high to cause the prosthesis core to soften, but not so high as to cause the prosthesis core to lose its overall shape or to cause the biocompatible metal powder to soften.

In some embodiments, the heated temperature is in a range of from 150 degrees Celsius to 200 degrees Celsius. In some embodiments, the heated temperature is in a range of from 150 degrees Celsius to 190 degrees Celsius. In some embodiments, the heated temperature is in a range of from 150 degrees Celsius to 180 degrees Celsius. In some embodiments, the heated temperature is in a range of from 150 degrees Celsius to 170 degrees Celsius. In some embodiments, the heated temperature is in a range of from 150 degrees Celsius to 160 degrees Celsius. In some embodiments, the heated temperature is in a range of from 160 degrees Celsius to 200 degrees Celsius. In some embodiments, the heated temperature is in a range of from 160 degrees Celsius to 190 degrees Celsius. In some embodiments, the heated temperature is in a range of from 160 degrees Celsius to 180 degrees Celsius. In some embodiments, the heated temperature is in a range of from 160 degrees Celsius to 170 degrees Celsius. In some embodiments, the heated temperature is in a range of from 170 degrees Celsius to 200 degrees Celsius. In some embodiments, the heated temperature is in a range of from 170 degrees Celsius to 190 degrees Celsius. In some embodiments, the heated temperature is in a range of from 170 degrees Celsius to 180 degrees Celsius. In some embodiments, the heated temperature is in a range of from 180 degrees Celsius to 200 degrees Celsius. In some embodiments, the heated temperature is in a range of from 180 degrees Celsius to 190 degrees Celsius. In some embodiments, the heated temperature is in a range of from 190 degrees Celsius to 200 degrees Celsius.

In some embodiments, the heating step includes placing the pressure vessel in a preheated environment (e.g., a preheated oven) that is preheated to the heated temperature before placement of the sealed pressure vessel. In some embodiments, the heating step includes gradually heating an environment in which the sealed pressure vessel is positioned from a lower temperature to the preheated temperature. For example, in some embodiments, the heating step includes placing the sealed pressure vessel in an environment that is at a lower temperature than the preheated temperature (e.g., is at room temperature, or is at an intermediate temperature that is between room temperature than the preheated temperature) and heating the environment from the lower temperature to the heated temperature.

In some embodiments, during the heating step, the contents of the pressure vessel (e.g., the prosthesis core and the biocompatible metal powder) are heated to the heated temperature in accordance with a controlled heating profile. In some embodiments, the controlled heating profile includes heating the environment at a controlled heating rate. In some embodiments in which the heating step includes placing the pressure vessel in a preheated environment that is preheated to the heated temperature, the contents of the pressure vessel gradually rise from an original temperature (e.g., room temperature) to the heated temperature at the controlled heating rate based on factors such as the thermal mass of the items being heated. In some embodiments in which the heating step includes gradually heating an environment in which the sealed pressure vessel is positioned from a lower temperature (e.g., room temperature) to the preheated temperature, the environment is heated at the controlled heating rate to thereby heat the sealed pressure vessel and the contents thereof at the controlled heating rate.

In some embodiments, the controlled heating rate is in a range of from 0.01 degrees Celsius per hour to 50 degrees Celsius per hour. In some embodiments, the controlled heating rate is in a range of from 0.01 degrees Celsius per hour to 40 degrees Celsius per hour. In some embodiments, the controlled heating rate is in a range of from 0.01 degrees Celsius per hour to 30 degrees Celsius per hour. In some embodiments, the controlled heating rate is in a range of from 0.01 degrees Celsius per hour to 20 degrees Celsius per hour. In some embodiments, the controlled heating rate is in a range of from 0.01 degrees Celsius per hour to 10 degrees Celsius per hour. In some embodiments, the controlled heating rate is in a range of from 10 degrees Celsius per hour to 50 degrees Celsius per hour. In some embodiments, the controlled heating rate is in a range of from 10 degrees Celsius per hour to 40 degrees Celsius per hour. In some embodiments, the controlled heating rate is in a range of from 10 degrees Celsius per hour to 30 degrees Celsius per hour. In some embodiments, the controlled heating rate is in a range of from 10 degrees Celsius per hour to 20 degrees Celsius per hour. In some embodiments, the controlled heating rate is in a range of from 20 degrees Celsius per hour to 50 degrees Celsius per hour. In some embodiments, the controlled heating rate is in a range of from 20 degrees Celsius per hour to 40 degrees Celsius per hour. In some embodiments, the controlled heating rate is in a range of from 20 degrees Celsius per hour to 30 degrees Celsius per hour. In some embodiments, the controlled heating rate is in a range of from 30 degrees Celsius per hour to 50 degrees Celsius per hour. In some embodiments, the controlled heating rate is in a range of from 30 degrees Celsius per hour to 40 degrees Celsius per hour. In some embodiments, the controlled heating rate is in a range of from 40 degrees Celsius per hour to 50 degrees Celsius per hour.

In step 160, the sealed pressure vessel is held at the heated temperature for a sufficient time period to adhere the biocompatible metal powder to the prosthesis core in a manner as will be described herein. In some embodiments, the sufficient time period is a predetermined time period. In some embodiments, the predetermined time period is a time period that is in a range of from 10 minutes to 600 minutes. In some embodiments, during step 160, the application of heat causes the prosthesis core both to soften and expand. In some embodiments, expansion of the prosthesis core, together with buildup of pressure within the pressure vessel in embodiments in which the pressure vessel is hermetically sealed, causes an increase pressure within the pressure vessel. In some embodiments, the pressure within the pressure vessel during step 160 is in a range of from 10 MPa to 50 MPa. In some embodiments, while the pressure vessel is held at the heated temperature and pressure builds within the pressure vessel, the titanium powder acts as a working fluid within the pressure vessel.

In some embodiments, during the sufficient time period during which the sealed pressure vessel is being held at the heated temperature, the prosthesis core softens and expands. As a result of the softening and expansion, together with the lack of head space surrounding the biocompatible metal powder and the incompressibility of the biocompatible metal powder, the prosthesis core expands into the gaps that are present between the surrounding particles of the biocompatible metal powder, thereby forcing a layer of the surrounding particles into the exterior of the prosthesis core and forming a coating. In some embodiments, the coating is formed on the entire exterior surface of the prosthesis core other than the contact area between the tool and the prosthesis core, which remains uncoated. In some embodiments, because the heated temperature is not sufficiently high to cause softening of the biocompatible metal powder, the particles that form the coating do not join or adhere to one another or otherwise form a unitary whole, but, rather, remain as discrete particles that adhere to the prosthesis core independently of one another.

In step 170, the sealed pressure vessel is allowed to cool to a step-down temperature at a controlled cooling rate. In some embodiments, the step-down temperature is a temperature that is between the heated temperature and an ambient temperature. In some embodiments, the controlled cooling allows a suitable crystalline structure to be maintained in the polymeric material of the prosthesis core. In some embodiments, during the controlled cooling, the prosthesis core resolidifies after having softened while at the heated temperature. In some embodiments, as the prosthesis core resolidifies, the particles of the biocompatible metal powder that have adhered to the prosthesis core remain adhered as a coating, and remain discrete particles that do not adhere to one another. In some embodiments, at the same time, the particles of the biocompatible metal powder that have not adhered to the prosthesis core also do not adhere to one another, and remain in a free powder form that can be removed from the prosthesis core and coating. In some embodiments, the controlled cooling step includes a cooling phase that is performed while the pressure vessel is maintained in a controlled environment, such as within an oven.

In some embodiments, the step-down temperature is in a range that is between 20 degrees Celsius and 100 degrees Celsius. In some embodiments, the step-down temperature is in a range that is between 20 degrees Celsius and 90 degrees Celsius. In some embodiments, the step-down temperature is in a range that is between 20 degrees Celsius and 80 degrees Celsius. In some embodiments, the step-down temperature is in a range that is between 20 degrees Celsius and 70 degrees Celsius. In some embodiments, the step-down temperature is in a range that is between 20 degrees Celsius and 60 degrees Celsius. In some embodiments, the step-down temperature is in a range that is between 20 degrees Celsius and 50 degrees Celsius. In some embodiments, the step-down temperature is in a range that is between 20 degrees Celsius and 40 degrees Celsius. In some embodiments, the step-down temperature is in a range that is between 20 degrees Celsius and 30 degrees Celsius. In some embodiments, the step-down temperature is in a range that is between 30 degrees Celsius and 100 degrees Celsius. In some embodiments, the step-down temperature is in a range that is between 30 degrees Celsius and 90 degrees Celsius. In some embodiments, the step-down temperature is in a range that is between 30 degrees Celsius and 80 degrees Celsius. In some embodiments, the step-down temperature is in a range that is between 30 degrees Celsius and 70 degrees Celsius. In some embodiments, the step-down temperature is in a range that is between 30 degrees Celsius and 60 degrees Celsius. In some embodiments, the step-down temperature is in a range that is between 30 degrees Celsius and 50 degrees Celsius. In some embodiments, the step-down temperature is in a range that is between 30 degrees Celsius and 40 degrees Celsius. In some embodiments, the step-down temperature is in a range that is between 40 degrees Celsius and 100 degrees Celsius. In some embodiments, the step-down temperature is in a range that is between 40 degrees Celsius and 90 degrees Celsius. In some embodiments, the step-down temperature is in a range that is between 40 degrees Celsius and 80 degrees Celsius. In some embodiments, the step-down temperature is in a range that is between 40 degrees Celsius and 70 degrees Celsius. In some embodiments, the step-down temperature is in a range that is between 40 degrees Celsius and 60 degrees Celsius. In some embodiments, the step-down temperature is in a range that is between 40 degrees Celsius and 50 degrees Celsius.

In some embodiments, the step-down temperature is in a range that is between 50 degrees Celsius and 100 degrees Celsius. In some embodiments, the step-down temperature is in a range that is between 50 degrees Celsius and 90 degrees Celsius. In some embodiments, the step-down temperature is in a range that is between 50 degrees Celsius and 80 degrees Celsius. In some embodiments, the step-down temperature is in a range that is between 50 degrees Celsius and 70 degrees Celsius. In some embodiments, the step-down temperature is in a range that is between 50 degrees Celsius and 60 degrees Celsius. In some embodiments, the step-down temperature is in a range that is between 60 degrees Celsius and 100 degrees Celsius. In some embodiments, the step-down temperature is in a range that is between 60 degrees Celsius and 90 degrees Celsius. In some embodiments, the step-down temperature is in a range that is between 60 degrees Celsius and 80 degrees Celsius. In some embodiments, the step-down temperature is in a range that is between 60 degrees Celsius and 70 degrees Celsius. In some embodiments, the step-down temperature is in a range that is between 70 degrees Celsius and 100 degrees Celsius. In some embodiments, the step-down temperature is in a range that is between 70 degrees Celsius and 90 degrees Celsius. In some embodiments, the step-down temperature is in a range that is between 70 degrees Celsius and 80 degrees Celsius. In some embodiments, the step-down temperature is in a range that is between 80 degrees Celsius and 100 degrees Celsius. In some embodiments, the step-down temperature is in a range that is between 80 degrees Celsius and 90 degrees Celsius. In some embodiments, the step-down temperature is in a range that is between 90 degrees Celsius and 100 degrees Celsius.

In some embodiments, the step-down temperature is about 20 degrees Celsius, or about 21 degrees Celsius, or about 22 degrees Celsius, or about 23 degrees Celsius, or about 24 degrees Celsius, or about 25 degrees Celsius, or about 26 degrees Celsius, or about 27 degrees Celsius, or about 28 degrees Celsius, or about 29 degrees Celsius. In some embodiments, the step-down temperature is about 30 degrees Celsius, or about 31 degrees Celsius, or about 32 degrees Celsius, or about 33 degrees Celsius, or about 34 degrees Celsius, or about 35 degrees Celsius, or about 36 degrees Celsius, or about 37 degrees Celsius, or about 38 degrees Celsius, or about 39 degrees Celsius. In some embodiments, the step-down temperature is about 40 degrees Celsius, or about 41 degrees Celsius, or about 42 degrees Celsius, or about 43 degrees Celsius, or about 44 degrees Celsius, or about 45 degrees Celsius, or about 46 degrees Celsius, or about 47 degrees Celsius, or about 48 degrees Celsius, or about 49 degrees Celsius. In some embodiments, the step-down temperature is about 50 degrees Celsius, or about 51 degrees Celsius, or about 52 degrees Celsius, or about 53 degrees Celsius, or about 54 degrees Celsius, or about 55 degrees Celsius, or about 56 degrees Celsius, or about 57 degrees Celsius, or about 58 degrees Celsius, or about 59 degrees Celsius. In some embodiments, the step-down temperature is about 60 degrees Celsius, or about 61 degrees Celsius, or about 62 degrees Celsius, or about 63 degrees Celsius, or about 64 degrees Celsius, or about 65 degrees Celsius, or about 66 degrees Celsius, or about 67 degrees Celsius, or about 68 degrees Celsius, or about 69 degrees Celsius. In some embodiments, the step-down temperature is about 70 degrees Celsius, or about 71 degrees Celsius, or about 72 degrees Celsius, or about 73 degrees Celsius, or about 74 degrees Celsius, or about 75 degrees Celsius, or about 76 degrees Celsius, or about 77 degrees Celsius, or about 78 degrees Celsius, or about 79 degrees Celsius. In some embodiments, the step-down temperature is about 80 degrees Celsius, or about 81 degrees Celsius, or about 82 degrees Celsius, or about 83 degrees Celsius, or about 84 degrees Celsius, or about 85 degrees Celsius, or about 86 degrees Celsius, or about 87 degrees Celsius, or about 88 degrees Celsius, or about 89 degrees Celsius. In some embodiments, the step-down temperature is about 90 degrees Celsius, or about 91 degrees Celsius, or about 92 degrees Celsius, or about 93 degrees Celsius, or about 94 degrees Celsius, or about 95 degrees Celsius, or about 96 degrees Celsius, or about 97 degrees Celsius, or about 98 degrees Celsius, or about 99 degrees Celsius, or about 100 degrees Celsius. In the above, "about" should be understood to a range of within plus or minus two degrees Celsius; for example, "about 90 degrees Celsius" should be understood to a range of between 88 degrees Celsius and 92 degrees Celsius.

In some embodiments, the controlled cooling rate is between 0.1 degrees Celsius per hour and 10 degrees Celsius per hour. In some embodiments, the controlled cooling rate is between 0.1 degrees Celsius per hour and 8 degrees Celsius per hour. In some embodiments, the controlled cooling rate is between 0.1 degrees Celsius per hour and 6 degrees Celsius per hour. In some embodiments, the controlled cooling rate is between 0.1 degrees Celsius per hour and 4 degrees Celsius per hour. In some embodiments, the controlled cooling rate is between 0.1 degrees Celsius per hour and 2 degrees Celsius per hour. In some embodiments, the controlled cooling rate is between 2 degrees Celsius per hour and 10 degrees Celsius per hour. In some embodiments, the controlled cooling rate is between 2 degrees Celsius per hour and 8 degrees Celsius per hour. In some embodiments, the controlled cooling rate is between 2 degrees Celsius per hour and 6 degrees Celsius per hour. In some embodiments, the controlled cooling rate is between 2 degrees Celsius per hour and 4 degrees Celsius per hour. In some embodiments, the controlled cooling rate is between 4 degrees Celsius per hour and 10 degrees Celsius per hour. In some embodiments, the controlled cooling rate is between 4 degrees Celsius per hour and 8 degrees Celsius per hour. In some embodiments, the controlled cooling rate is between 4 degrees Celsius per hour and 6 degrees Celsius per hour. In some embodiments, the controlled cooling rate is between 6 degrees Celsius per hour and 10 degrees Celsius per hour. In some embodiments, the controlled cooling rate is between 6 degrees Celsius per hour and 8 degrees Celsius per hour. In some embodiments, the controlled cooling rate is between 8 degrees Celsius per hour and 10 degrees Celsius per hour.

In step 180, the sealed pressure vessel is allowed to cool to an ambient temperature. In some embodiments, the cooling to ambient temperature includes cooling in a manner that is not controlled to be at any particular rate of cooling (e.g., at an uncontrolled cooling rate). In some embodiments, the cooling to an ambient temperature includes removing the sealed pressure vessel from a controlled environment, such as an oven, and allowing the sealed pressure vessel to cool to ambient temperature in a non-controlled environment, such as within a room (e.g., cooling to room temperature). In some embodiments, step 180 is omitted, and instead the sealed pressure vessel is cooled from the heated temperature to an ambient temperature entirely in a controlled manner and at a controlled cooling rate.

In step 190, the sealed pressure vessel is unsealed, and the coated prosthesis core is removed from the pressure vessel. In some embodiments, the particles of the biocompatible metal powder that have not adhered to the prosthesis core during the heated stage remain unaggregated as described above, and are removed from the pressure vessel prior to removing the coated prosthesis core. In some embodiments, the unaggregated particles of the biocompatible metal are suitable for re-use in a subsequent performance of the method 100.

Figure 5:
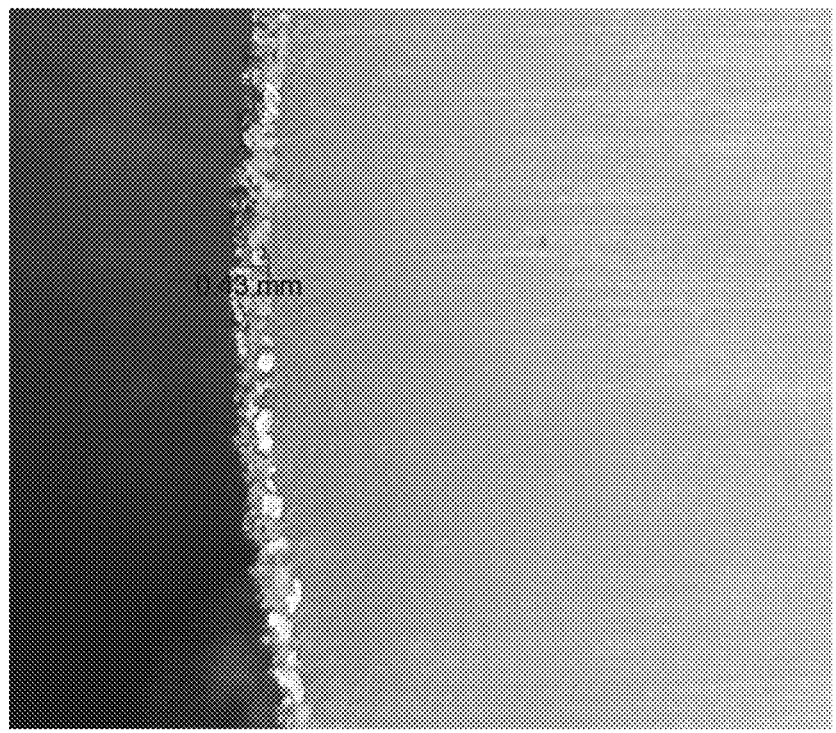
FIG. 5 shows an exemplary coated prosthesis core fabricated in accordance with an exemplary method, the coated prosthesis core having been cut transverse to the coating to show a cross-section of the coating, in accordance with some embodiments of the invention.
Figure 6:
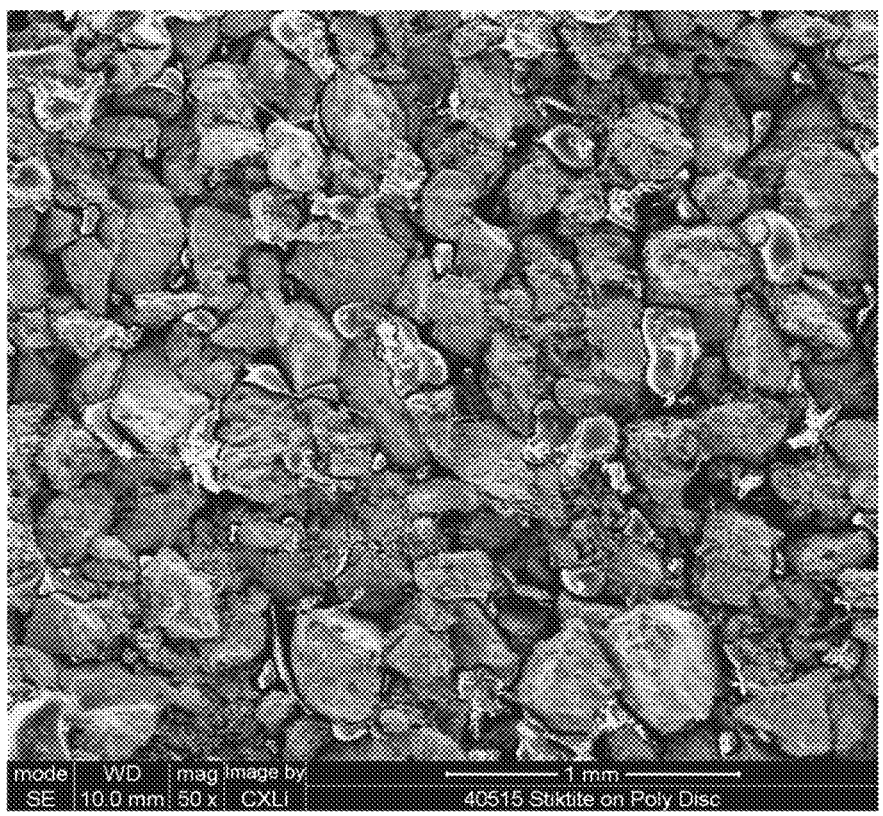
FIG. 6 shows an SEM image of an exemplary coating formed in accordance with an exemplary method in accordance with some embodiments of the invention.

Following step 190, the method 100 is complete. In some embodiments, the method 100 produces a prosthesis that includes a prosthesis core formed of a polymeric material, such as UHMWPE, having a coating formed from a biocompatible metal powder, such as titanium, and having an uncoated region that is sized and shaped to form an articular surface of the prosthesis. In some embodiments, as described above, the individual particles of the biocompatible metal powder that form the coating do not adhere to one another. FIG. 5 shows a portion of a coated prosthesis core, having been cut perpendicular to the coating to show a cross-section of the coating, in accordance with some embodiments of the invention. FIG. 6 shows a SEM view of a portion of an exemplary coating demonstrating that the particles do not adhere to one another to form a unitary whole, but, rather, remain as discrete particles, in accordance with some embodiments of the invention. In some embodiments, as a result of the formation of a coating formed from the biocompatible metal particles, the coating provides a surface that is conducive to bone ingrowth to facilitate implantation of the prosthesis. Additionally, as a result of the lack of aggregation among the individual particles that form the coating, the coating does not act as a single rigid layer, but, rather, allows the prosthesis to retain flexibility similar to that of the uncoated polymeric material of the core.

Figure 7:
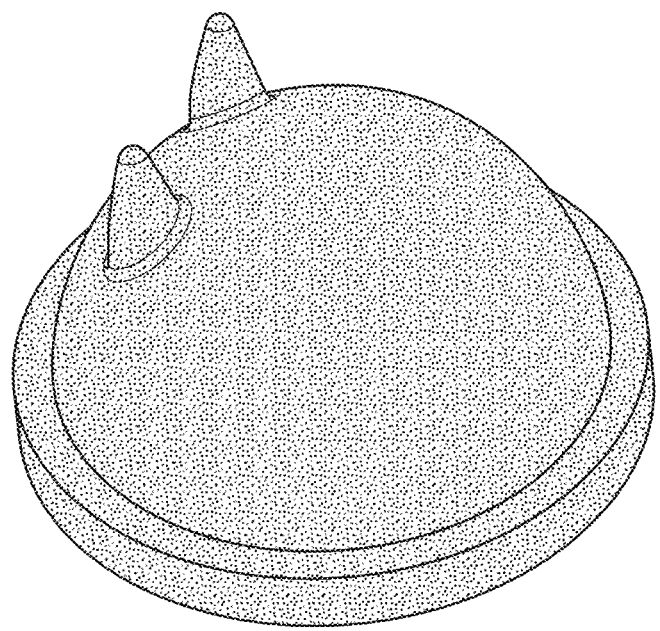
FIG. 7 shows an exemplary acetabular cup prosthesis fabricated in accordance with an exemplary method in accordance with some embodiments of the invention.
Figure 8:
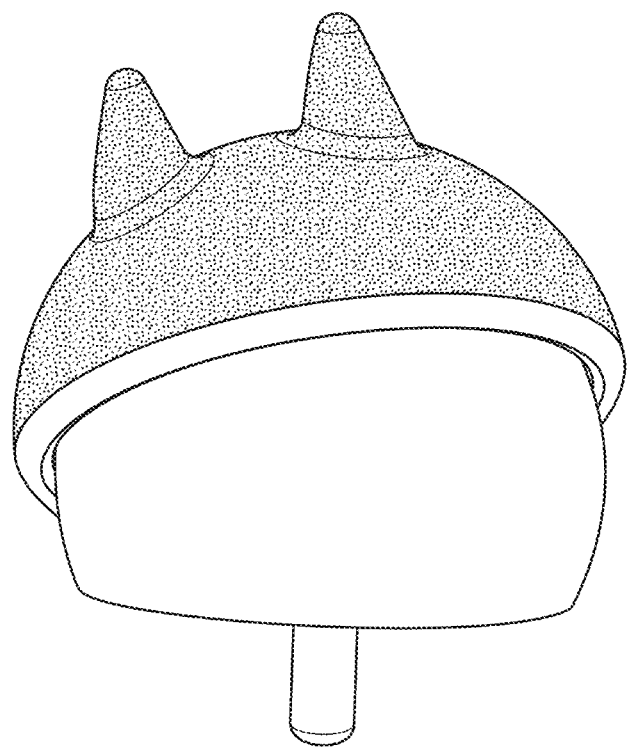
FIG. 8 shows an exemplary acetabular cup prosthesis fabricated in accordance with an exemplary method, as positioned to articulate with a representative prosthetic femoral head, in accordance with some embodiments of the invention.

In some embodiments, due to the adherence between the biocompatible metal powder and the prosthesis core, the coating that is formed on the coated prosthesis core provides advantageous mechanical properties, such as coating thickness, abrasion resistance, shear bond strength, and tensile bond strength, that cause the prosthesis formed from the prosthesis core and the coating to be durable when implanted in the body and to facilitate bone ingrowth into the coating. Additionally, in some embodiments, due to the fact that the particles of the biocompatible metal powder do not adhere to one another to form a unitary whole, and due to the controlled heating and cooling, the polymer core retains the flexibility of the uncoated polymer material. FIG. 7 shows a perspective view of an exemplary acetabular cup prosthesis fabricated in accordance with the techniques described herein. In some embodiments, an exemplary acetabular cup prosthesis is configured for use in a hip resurfacing procedure (e.g., to articulate with a patient's native femoral head). In some embodiments, an exemplary acetabular cup prosthesis is configured for use in a total hip replacement procedure (e.g., to articulate with a prosthetic femoral head). FIG. 8 shows an exemplary acetabular cup prosthesis fabricated in accordance with the techniques described herein, as positioned to articulate with a representative prosthetic femoral head.

In some embodiments, a prosthesis formed in accordance with the exemplary techniques described herein, when tested for abrasion resistance in accordance with ASTM F1978-22, loses less than 65 milligrams of its coating (e.g., between 20 milligrams and 65 milligrams) when abraded for 100 cycles, thereby satisfying FDA guidance for testing metallic plasma sprayed coatings on orthopedic implants. In some embodiments, a prosthesis formed in accordance with the exemplary techniques described herein has a static shear bond strength between its coating and its core of at least 15 MPa (e.g., in a range of from 15 MPa to 25 MPa) when tested in accordance with ISO13779-2:2018, with no value less than 10 MPa, thereby satisfying the standard for shear strength described in ISO13779-2:2018. In some embodiments, a prosthesis formed in accordance with the techniques described herein exhibits a tensile bond strength between its coating and its core at least 14 MPa (e.g., between 14 MPa and 25 MPa) when tested by a test method as described in, or generally in accordance with, the test method described in ASTM F1147-05. In some embodiments, prostheses formed in accordance with the techniques described herein exhibits a mean tensile bond strength that is at least 15 MPa with no values less than 10 MPa when tested by a test method as described in, or generally in accordance with, the test method described in ASTM F1147-05, thereby satisfying the standard for tensile bond strength described in ISO 13779-2:2018. In some embodiments, the core of a prosthesis formed in accordance with the techniques as described herein has a tensile strength that is from 35 MPa to 50 MPa when tested in accordance with ASTM D638-22. In some embodiments, the core of a prosthesis formed in accordance with the techniques as described herein has a compressive modulus that is from 0.8 GPa to 1.2 GPa when tested in accordance with ASTM D695-15.

In some embodiments, a prosthesis formed in accordance with the techniques described herein has a coating thickness (e.g., as measured at the center of the prosthesis similar to the thickness of the prosthesis core as described above) of between 300 microns and 550 microns. As noted above, in some embodiments, a prosthesis core of a prosthesis formed in accordance with the techniques described herein has a thickness of 5 millimeters to 9 millimeters, depending on the size of the prosthesis. Consequently, in some embodiments, the combined thickness of the prosthesis (e.g., including the prosthesis core and the coating) is in the range of 5,300 microns to 9,550 microns. In some embodiments, the relatively thin overall thickness of the prosthesis is material to the suitability of the prosthesis for use in joint resurfacing, due to being able to provide a sufficiently large concave space within the prosthesis core to accommodate a patient's native femoral head, while not requiring an excessive amount of tissue to be reamed from the patient's pelvis to accommodate the prosthesis due to the relatively thin thickness of the prosthesis.

In some embodiments, a prosthesis formed in accordance with the techniques described herein has a coating thickness of between 300 microns and 550 microns. In some embodiments, a prosthesis has a coating thickness of between 300 microns and 500 microns. In some embodiments, a prosthesis has a coating thickness of between 300 microns and 450 microns. In some embodiments, a prosthesis has a coating thickness of between 300 microns and 400 microns. In some embodiments, a prosthesis has a coating thickness of between 300 microns and 350 microns. In some embodiments, a prosthesis has a coating thickness of between 350 microns and 550 microns. In some embodiments, a prosthesis has a coating thickness of between 350 microns and 500 microns. In some embodiments, a prosthesis has a coating thickness of between 350 microns and 450 microns. In some embodiments, a prosthesis has a coating thickness of between 350 microns and 400 microns. In some embodiments, a prosthesis has a coating thickness of between 400 microns and 550 microns. In some embodiments, a prosthesis has a coating thickness of between 400 microns and 500 microns. In some embodiments, a prosthesis has a coating thickness of between 400 microns and 450 microns. In some embodiments, a prosthesis has a coating thickness of between 450 microns and 550 microns. In some embodiments, a prosthesis has a coating thickness of between 450 microns and 500 microns. In some embodiments, a prosthesis has a coating thickness of between 550 microns and 550 microns.

In some embodiments, a prosthesis core of a prosthesis formed in accordance with the techniques described herein has a thickness of 5 millimeters to 9 millimeters. In some embodiments, a prosthesis core has a thickness of 5 millimeters to 8 millimeters. In some embodiments, a prosthesis core has a thickness of 5 millimeters to 7 millimeters. In some embodiments, a prosthesis core has a thickness of 5 millimeters to 6 millimeters. In some embodiments, a prosthesis core has a thickness of 6 millimeters to 9 millimeters. In some embodiments, a prosthesis core has a thickness of 6 millimeters to 8 millimeters. In some embodiments, a prosthesis core has a thickness of 6 millimeters to 7 millimeters. In some embodiments, a prosthesis core has a thickness of 7 millimeters to 9 millimeters. In some embodiments, a prosthesis core has a thickness of 7 millimeters to 8 millimeters. In some embodiments, a prosthesis core has a thickness of 8 millimeters to 9 millimeters.

In some embodiments a prosthesis formed in accordance with the techniques described herein has a combined thickness (e.g., including the respective thicknesses of prosthesis core and the coating) in the range of 5,300 microns to 9,550 microns. In some embodiments, the combined thickness is from 5,300 microns to 8,500 microns. In some embodiments, the combined thickness is from 5,300 microns to 7,500 microns. In some embodiments, the combined thickness is from 5,300 microns to 6,500 microns. In some embodiments, the combined thickness is from 6,500 microns to 9,550 microns. In some embodiments, the combined thickness is from 6,500 microns to 8,500 microns. In some embodiments, the combined thickness is from 6,500 microns to 7,500 microns. In some embodiments, the combined thickness is from 7,500 microns to 9,550 microns. In some embodiments, the combined thickness is from 7,500 microns to 8,500 microns. In some embodiments, the combined thickness is from 8,500 microns to 9,550 microns.

In some embodiments, a device includes a core and a coating layer, wherein the core is a cup-shaped core having a first side and a second side, wherein the first side is concave, and wherein the second side is convex, wherein the core includes ultra-high molecular weight polyethylene, wherein the ultra-high molecular weight polyethylene has a weight average molecular weight that is in a range of from $2\times10^6$ grams per mole to $3\times10^6$ grams per mole, wherein, when tested in accordance with ASTM D638-22, the core has a tensile strength that is in a range of from 35 MPa to 50 MPa, and wherein, when tested in accordance with ASTM D695-15, the core has a compressive modulus that is in a range of from 0.8 GPa to 1.2 GPa; wherein the coating layer coats the second side of the core, wherein the coating layer includes titanium powder, wherein the titanium powder has a D50 particle size of 225 microns, wherein the coating layer has a mean thickness that is in a range of from 300 to 550 microns, wherein the device is an acetabular cup prosthesis, wherein, when tested for abrasion resistance in accordance with ASTM F1978-22, the coating layer loses less than 65 milligrams when abraded for 100 cycles, wherein, when tested for static shear bond strength in accordance with ISO13779-2:2018, the coating layer has a static shear bond strength that is in a range of from 15 MPa to 25 MPa, and wherein, when tested for static tensile bond strength in accordance with ASTM F1147-05, the coating layer has a static tensile bond strength that is in a range of from 14 MPa to 25 MPa.

In some embodiments, a method for producing a prosthesis includes fabricating a prosthesis core from a core material, wherein the core material comprises ultra-high molecular weight polyethylene, wherein the ultra-high molecular weight polyethylene has a weight average molecular weight that is in a range of from $2\times10^6$ grams per mole to $3\times10^6$ grams per mole; positioning the prosthesis core within a pressure vessel, wherein the prosthesis core has a prosthesis core height within the pressure vessel; filling the pressure vessel with titanium powder, wherein the titanium powder has a D50 particle size of 225 microns, wherein the titanium powder is filled to at least 110% of the core height; sealing the pressure vessel, wherein the sealing the pressure vessel comprises positioning a pressure plate in contact with the titanium powder; maintaining the pressure vessel at a temperature that is in a range of from 150 degrees Celsius to 200 degrees Celsius and a pressure that is in a range of from 10 MPa to 50 MPa for a time period that is in a range of from 10 minutes to 600 minutes, cooling the pressure vessel to room temperature, wherein the cooling includes a controlled cooling phase in which the pressure vessel is cooled from the heated temperature to a step-down temperature at a controlled cooling rate, wherein the controlled cooling rate is in a range of from 0.1 degrees Celsius per hour to 10 degrees Celsius per hour, wherein the method produces an acetabular cup prosthesis including the prosthesis core and a coating layer, wherein the prosthesis core is a cup-shaped core having a first side and a second side, wherein the first side is concave, and wherein the second side is convex, wherein the coating layer coats the second side of the core, wherein the coating layer includes the titanium powder, and wherein the coating layer has a mean thickness that is in a range of from 300 to 550 microns, wherein, when tested for abrasion resistance in accordance with ASTM F1978-22, the coating layer loses less than 65 milligrams when abraded for 100 cycles, wherein, when tested for static shear bond strength in accordance with ISO13779-2:2018, the coating layer has a static shear bond strength that is in a range of from 15 MPa to 25 MPa, and wherein, when tested for static tensile bond strength in accordance with ASTM F1147-05, the coating layer has a static tensile bond strength that is in a range of from 15 MPa to 25 MPa.

The terminology used herein is intended to describe embodiments and is not intended to be limiting. The terms "a," "an," and "the" include the plural forms as well, unless clearly indicated otherwise. The terms "comprises" and/or "comprising," when used in this Specification, specify the presence of the stated features, integers, steps, operations, elements, and/or components, but do not preclude the presence or addition of one or more other features, integers, steps, operations, elements, and/or components. Ranges described herein are inclusive, i.e., a range of 5 to 10 includes 5, 10, and all values therebetween.

It is to be understood that changes may be made in detail, especially in matters of the construction materials employed and the shape, size, and arrangement of parts without departing from the scope of the present disclosure. This Specification and the embodiments described are examples, with the true scope and spirit of the disclosure being indicated by the claims that follow.

What is claimed is:

1. A method for producing a prosthesis, the method comprising:
fabricating a prosthesis core from a core material,
wherein the core material comprises ultra-high molecular weight polyethylene,
wherein the ultra-high molecular weight polyethylene has a weight average molecular weight that is in a range of from $2\times10^6$ grams per mole to $3\times10^6$ grams per mole;
positioning the prosthesis core within a pressure vessel,
wherein the prosthesis core has a prosthesis core height within the pressure vessel;
filling the pressure vessel with titanium powder,
wherein the titanium powder has a D50 particle size that is in a range of from 200 microns to 250 microns, and
wherein the titanium powder is filled to at least 110% of the core height;
sealing the pressure vessel,
wherein the sealing the pressure vessel comprises positioning a pressure plate in contact with the titanium powder;
maintaining the pressure vessel at a heated temperature that is in a range of from 150 degrees Celsius to 200 degrees Celsius and a pressure that is in a range of from 10 MPa to 50 MPa for a time period that is in a range of from 10 minutes to 600 minutes;
cooling the pressure vessel to room temperature, wherein the cooling comprises:

a controlled cooling phase in which the pressure vessel is cooled from the heated temperature to a step-down temperature at a controlled cooling rate,
wherein the controlled cooling rate is in a range of from 0.1 degrees Celsius per hour to 10 degrees Celsius per hour,
wherein the method produces the prosthesis comprising the prosthesis core and a coating comprising the titanium powder.

2. The method of claim 1, wherein the step of sealing the pressure vessel comprises hermetically sealing the pressure vessel such that gases cannot enter or exit the pressure vessel.

3. The method of claim 1, wherein the step of sealing the pressure vessel comprises non-hermetically sealing the pressure vessel such that gases can enter and exit the pressure vessel.

4. The method of claim 1, wherein, after sealing the pressure vessel, the titanium powder acts as a working fluid within the pressure vessel.

5. The method of claim 1, wherein the step-down temperature is in a range of from an ambient temperature to 70 degrees Celsius.

6. The method of claim 1, wherein the cooling further comprises a second cooling phase in which the pressure vessel is cooled from the step-down temperature to an ambient temperature at an uncontrolled cooling rate.

7. The method of claim 1, wherein at least a portion of the prosthesis core is sized and shaped to form an articular portion of one of an acetabular cup prosthesis, a shoulder prosthesis, a knee prosthesis, an ankle prosthesis, or a toe joint prosthesis.

8. The method of claim 7, wherein the articular portion of the acetabular cup prosthesis is sized to articulate with a patient's native femoral head.

9. The method of claim 7, wherein the articular portion of the acetabular cup prosthesis is sized to articulate with a prosthetic femoral head of a total hip replacement prosthetic joint.

10. The method of claim 1, wherein the step of maintaining the pressure vessel at the heated temperature comprises maintaining the pressure vessel in an oven that is at the heated temperature.

11. The method of claim 10, further comprising preheating the oven to the heated temperature and placing the pressure vessel in the preheated oven prior to maintaining the pressure vessel at the heated temperature.

12. The method of claim 1, wherein the ultra-high molecular weight polyethylene is vitamin E-enriched.

13. The method of claim 1, wherein a thickness of the prosthesis core is in a range of from 5 millimeters to 9 millimeters.

14. The method of claim 13, wherein a thickness of the coating is in a range of from 300 microns to 550 microns.

15. The method of claim 1, wherein particles of the titanium powder that form the coating do not adhere to one another to form a unitary whole.

16. The method of claim 1, wherein the titanium powder has a D50 particle size that is 225 microns.

* * * * *